United States Patent
Lange

[11] Patent Number: 5,709,646
[45] Date of Patent: Jan. 20, 1998

[54] SURGICAL RETRACTOR COVERS

[76] Inventor: Nancy Erin Lange, 108 N. Walnut St., Maquoketa, Iowa 52060

[21] Appl. No.: 647,782

[22] Filed: May 15, 1996

Related U.S. Application Data

[63] Continuation-in-part of Ser. No. 311,650, Sep. 23, 1994, abandoned.

[51] Int. Cl.$^6$ .................................................. A61B 17/02
[52] U.S. Cl. .................................................. 600/203; 606/1
[58] Field of Search .................................. 600/203, 201, 600/226, 186, 220, 195, 197; 606/1

[56] References Cited

U.S. PATENT DOCUMENTS

| | | | |
|---|---|---|---|
| 3,867,927 | 2/1975 | Hergott | 600/203 X |
| 3,882,855 | 5/1975 | Schulte et al. | 600/206 |
| 4,615,334 | 10/1986 | Jaeger | 600/220 X |
| 4,972,825 | 11/1990 | Vescovo, Jr. | 600/186 |
| 5,007,409 | 4/1991 | Pope | 600/203 |
| 5,558,665 | 9/1996 | Kieturakis | 606/1 |
| 5,624,381 | 4/1997 | Kieturakis | 600/206 |

*Primary Examiner*—Jeffrey A. Smith
*Attorney, Agent, or Firm*—Henderson & Sturm

[57] ABSTRACT

The present invention teaches an elastic, sterile and disposable cover pad which can be secured over surgical retractors to reduce slipping of the retractor in the body cavity and reduce trauma to tissue. The invention can also be secured over the handle end of hand-held retractors to ease the workload on surgical personnel who are required to hold the retractors for extended periods of time.

6 Claims, 4 Drawing Sheets

SURGICAL RETRACTOR COVERS

This is a continuation-in-part application of patent application Ser. No. 08/311,650 filed on Sep. 23, 1994 and entitled "Surgical Retractor Covers"(now abandoned).

TECHNICAL FIELD

The present invention relates to the field of medical instruments, particularly to surgical retractors, and more particularly to an elastic, sterile, disposable retractor cover.

BACKGROUND ART

Modern surgery requires adequate exposure in the surgical area to provide sufficient visual and physical access to the organs. This is ordinarily accomplished by the use of hand-held or self-retaining retractors comprised of a blade area for engaging the tissue at the point of incision, a retention means, and a shank which connects the blade to the retention means. The retractor blades come in a multitude of shapes and sizes depending upon the surgical procedure to be performed. There are also a multitude of retention means which range from self-retaining devices to handles, the numerous shapes of which have been dictated by the preferences of surgical nurses and assistants.

Surgical retractors are generally made from stainless steel because of its strength and its ability to be sterilized. The retractors are therefore extremely hard and become very slippery when they come into contact with blood and other bodily fluids during the surgical procedures. This hardness also often results in tissue damage and bruising due to the pressure that must be exerted during retraction of these tissues. Stainless steel is also thermally highly conductive and quickly absorbs heat from the tissue with which it comes into contact, often resulting in tissue injury. A further disadvantage of standard stainless steel retractors is that their reflective surfaces produce glare under the high level illumination typical during surgical procedures.

The correct use of a hand-held retractor requires that it be held by its handle to produce maximum exposure of the surgical area, maximum leverage, and steady retraction. Since surgical procedures often take several hours, surgical nurses and assistants who are required to hold the retractors can become very fatigued since the retractor handles can also become slippery and difficult to hold onto. They are also very uncomfortable because of their hardness.

In an effort to alleviate some of these many disadvantages of stainless steel retractors, nurses often wrap the retractors with gauze which is then held in place with rubber bands or tape. This procedure is minimally effective at best, and can cause complications if the wrapping comes apart and spills within the body cavity.

DISCLOSURE OF THE INVENTION

The present invention teaches a novel disposable, elastic, sterile sheath which can be secured over the blade of surgical retractors to reduce slipping of the retractor in the body cavity, reduce trauma to tissue, and reduce glare. The invention can also be secured over the handle end of hand-held retractors to ease the workload on surgical personnel who are required to hold the retractors for extended periods of time.

In addition, this invention is fabricated in such a manner that the ultimate exterior surface of the sheath is maintained in a sterile condition up to and during the deployment of the sheath on the medical instrument so that the likelihood of the exterior surface of the sheath becoming contaminated prior to usage is virtually eliminated.

BRIEF DESCRIPTION OF THE DRAWINGS

These and other attributes of the invention will become more clear upon a thorough study of the following description of the best mode for carrying out the invention, particularly when reviewed in conjunction with the drawings, wherein.

BEST MODE FOR CARRYING OUT THE INVENTION

Figure 2:
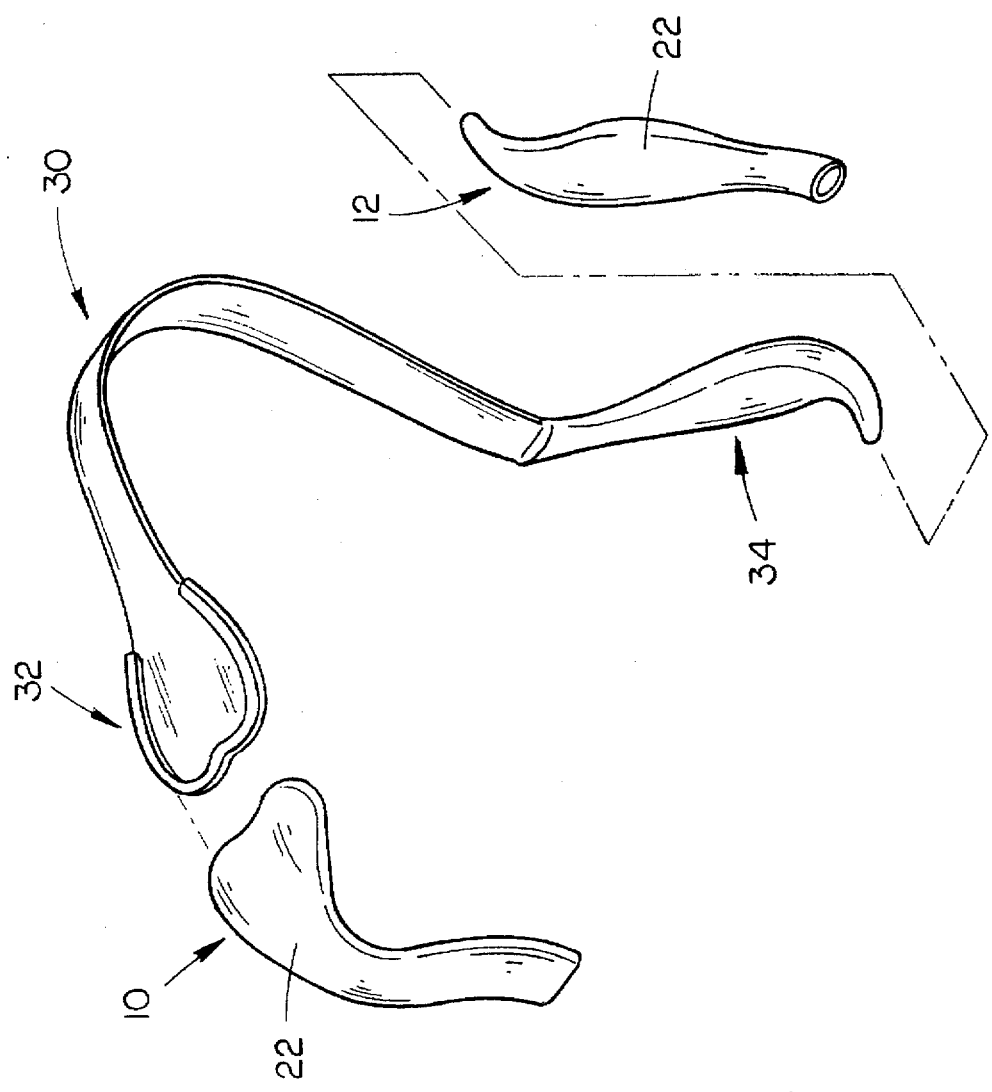
FIG. 2 is a perspective view of a first and second embodiment of the invention just prior to placement on a typical surgical retractor.
Figure 1:
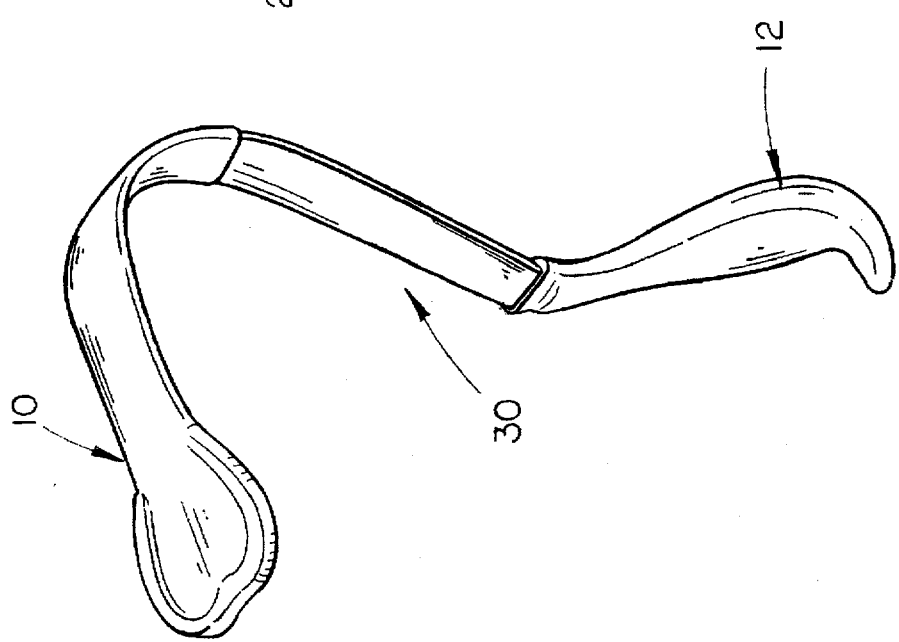
FIG. 1 is a perspective view of a first and second embodiment of the invention in place on a typical hand-held surgical retractor.
Figure 3:
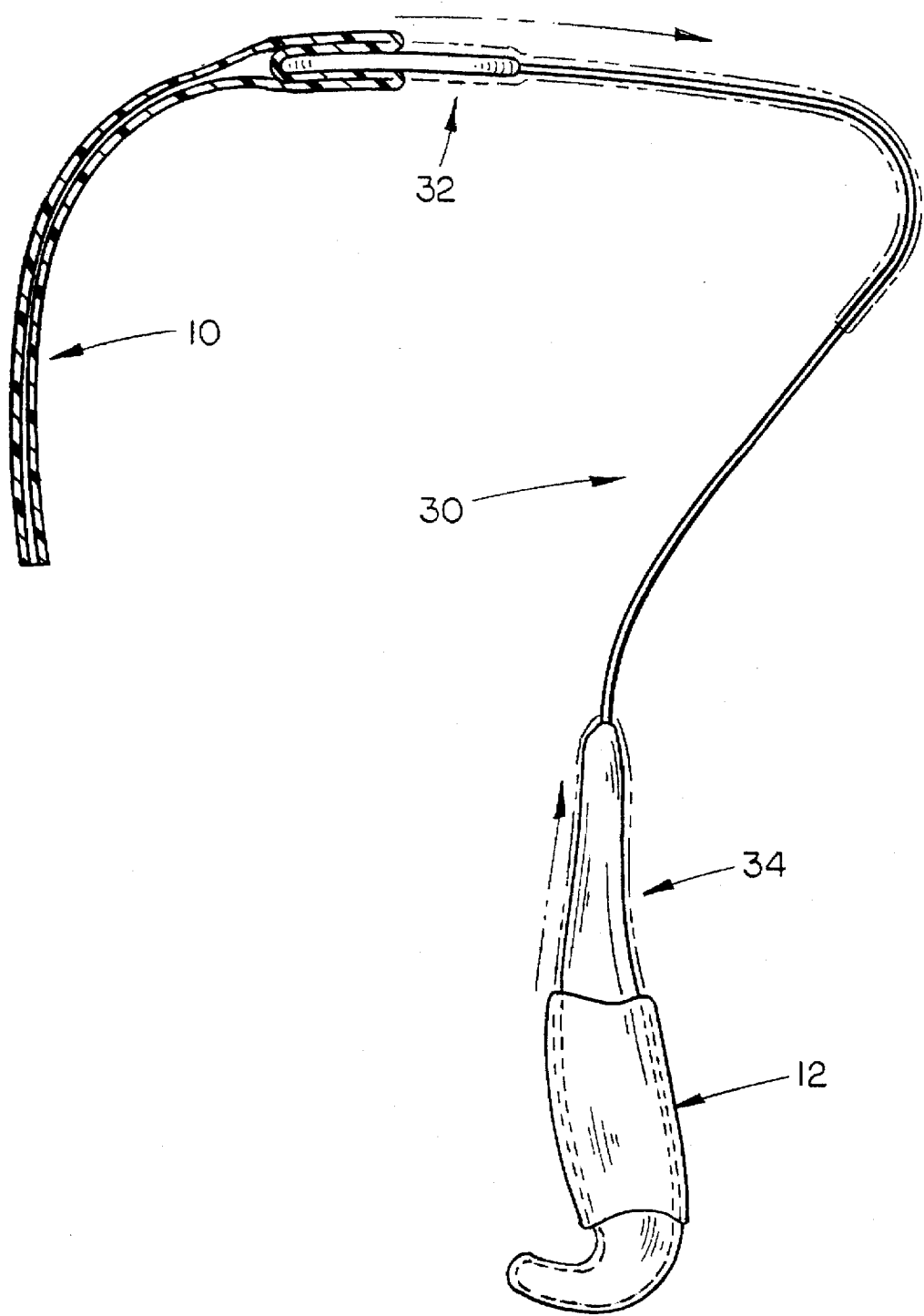
FIG. 3 is a side elevational view, in partial section, showing the invention being rolled onto a typical surgical retractor.

Referring now to the drawings, first and second embodiments of the invention 10 and 12 are depicted in FIG. 1 and FIG. 2 with a typical, surgical hand-held retractor 30. The retractor covers 10 and 12 are preferably fabricated from silicone, although other plastic or rubber products having the requisite elasticity may also be suitable. As is most clearly depicted in FIG. 2, the retractor covers 10, 12 are comprised of an essentially tubular sheath having a shape somewhat in conformity with the retractor with which they are to be used and having a thickness of approximately one-sixteenth to one-eight of an inch. For hand-held retractors, there will be a pair of retractor covers available; one for the blade end 32 of the retractor and one for the handle end 34 of the retractor.

The covers 10, 12 are initially inside-out and, in a preferred embodiment, are provided with an adhesive coating 22 on the side which will be in contact with the retractor after placement thereon. This adhesive aids in maintaining the cover on the retractor during the surgical procedure, but does not interfere with the removal of the cover when the procedure is complete.

Figure 6:
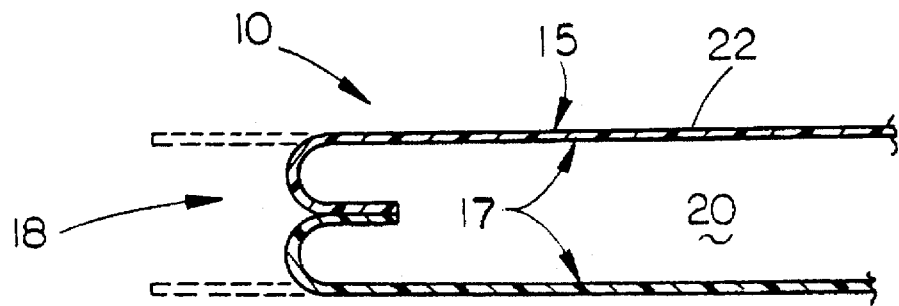
FIG. 6 is an isolated cross-sectional detail view of the sealed end of the sheath.
Figure 7:
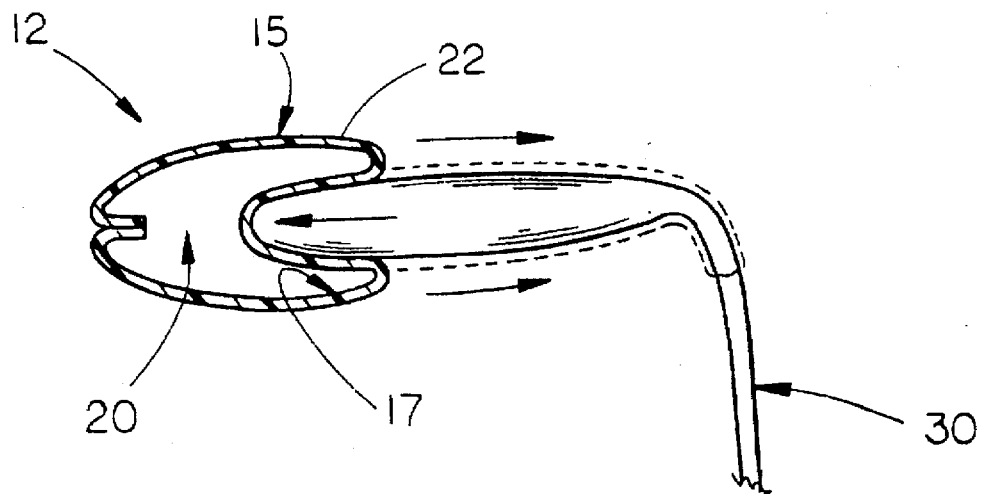
FIG. 7 is a cross sectional view depicting the engagement of the medical instrument and the sheath just prior to the rupturing of the sealed end of the sheath.

As can be seen by reference to FIGS. 6, and 7, each of the covers 10 and 12 have an ultimate interior surface 15 which is provided with an adhesive coating 22 and an ultimate exterior surface 17 which must be maintained in a sterile condition prior to being deployed on a medical instrument 30.

As can best be appreciated by reference to FIGS. 6 and 7 when each cover 10 and 12 is initially manufactured, the ultimate interior surface 15 is disposed on the exterior of the respective cover 10 and 12 and the adhesive coating 22 is applied thereto. Then the open end 18 of each cover 10 and 12 is sealed by inverting the opposed adhesive coated surfaces and bringing them into contact with one another as shown in FIG. 6 to essentially form a sterile interior chamber 20 whose purpose and function will be described presently.

Turning now to FIG. 7, it can be seen that the installation of each cover 10 and 12 begins by engaging one end of the medical instrument 30 with the end of one of the covers 12 opposite the sealed opening 18. As the leading edge of the medical instrument 30 is progressively covered by the cover 12, the closer the leading edge comes to the sealed opening 18, until finally the leading edge will rupture the sealed opening 18 and pass through the opening 18 to complete the installation of the cover 12 on one end of the medical instrument.

By now it should be appreciated that the integrity of the sterile chamber 20 is maintained up to the point that the cover 12 is substantially deployed on one end of the medical instrument 30 and that the sterile condition of both covers 10 and 12 are maintained up to the last possible moment when they are engaged on the opposite ends of the medical instrument 30.

When the surgical procedure is complete, the cover is rolled back off of the retractor and is discarded.

Figure 5:
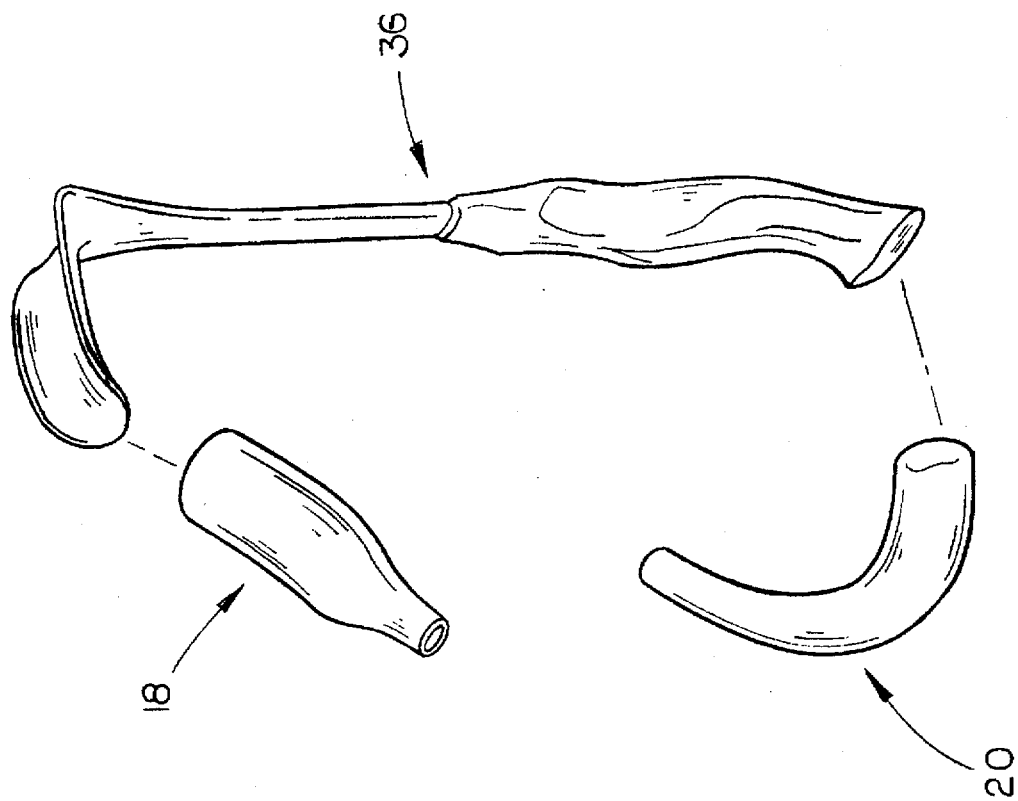
FIG. 5 is a perspective view of a fifth and sixth embodiment of the invention.
Figure 4:
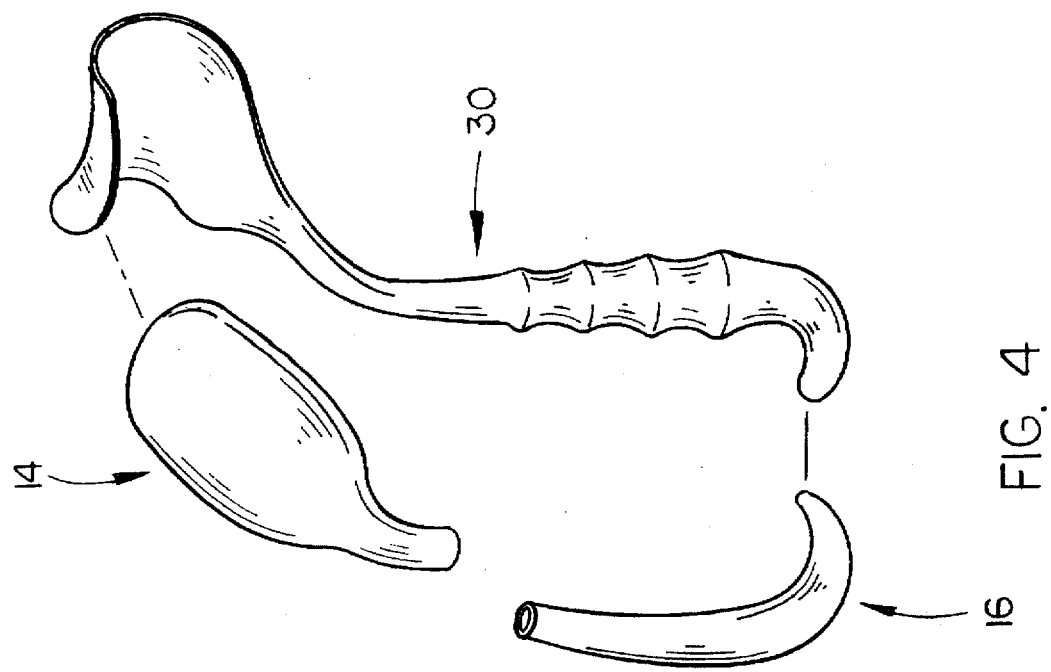
FIG. 4 is a perspective view of a third and fourth embodiment of the invention.

FIG. 4 and FIG. 5 depict further embodiments 14, 16, 18, 20 of covers for use with different types of surgical retractors 30, 36.

Those skilled in the art will recognize that many modifications and variations of the present invention are possible in light of the above teachings. It is therefore to be understood that, within the scope of the appended claims, the invention may be practiced otherwise than as specifically described.

I claim:

1. An apparatus for padding at least one end of a medical instrument comprising:

a sterile generally tubular sheath dimensioned to envelope one end of the medical instrument; wherein, the tubular sheath has an open end, a closed end, an initial interior surface which becomes the ultimate exterior surface and an initial exterior surface which becomes the ultimate interior surface when the sheath is operatively deployed on said medical instrument; and an adhesive coating formed on the initial exterior surface; wherein, the adhesive coated surface surrounding the open end of the tubular sheath are joined together to form a sterile interior chamber in the sheath defined by the initial interior surface.

2. The apparatus as in claim 1 wherein said tubular sheath is elastic.

3. The apparatus as in claim 1 wherein said tubular sheath is fabricated from silicone.

4. An apparatus for padding the opposite ends of a medical instrument comprising:

a pair of sterile generally tubular sheaths wherein each sheath is dimensioned to envelope one end of the medical instrument; and wherein, each tubular sheath has an open end, a closed end, an initial interior surface which becomes the ultimate exterior surface and an initial exterior surface which becomes the ultimate interior surface when the sheath is operatively deployed on one end of said medical instrument; and an adhesive coating formed on the initial exterior surface of each sheath; wherein, the adhesive coated surface surrounding the open end of the tubular sheath are joined together to form a sterile interior chamber in the sheath defined by the initial interior surface.

5. The apparatus as in claim 4; wherein, each tubular sheath is elastic.

6. The apparatus as in claim 4; wherein, each tubular sheath is fabricated from silicone.

* * * * *